United States Patent [19]

Carter

[11] Patent Number: 5,006,120

[45] Date of Patent: Apr. 9, 1991

[54] DISTAL RADIAL FRACTURE SET AND METHOD FOR REPAIRING DISTAL RADIAL FRACTURES

[76] Inventor: Peter R. Carter, 3707 Gaston Ave., Suite 520, Dallas, Tex. 75246

[21] Appl. No.: 418,582

[22] Filed: Oct. 10, 1989

[51] Int. Cl.$^5$ .............................................. A61F 5/04
[52] U.S. Cl. ...................................... 606/69; 606/71; 606/72
[58] Field of Search ................................. 606/69–75; 128/92 YV, 92 YP

[56] References Cited

U.S. PATENT DOCUMENTS

| Re. 31,628 | 7/1984 | Allgower et al. | 606/69 |
|---|---|---|---|
| 2,511,051 | 6/1950 | Dzus | 606/73 |
| 2,526,959 | 10/1950 | Lorenzo | 606/71 |
| 3,025,853 | 3/1962 | Mason | 128/92 R |
| 3,334,624 | 8/1967 | Schneider et al. | 606/62 |
| 3,489,143 | 1/1970 | Halloran | 606/72 |
| 3,552,389 | 1/1971 | Allgower et al. | 606/69 |
| 3,716,050 | 2/1973 | Johnston | 606/69 |
| 3,824,995 | 7/1974 | Getscher | 606/69 |
| 3,939,498 | 2/1976 | Lee | 128/92 YP |
| 4,101,985 | 7/1978 | Baumann | 128/92 YV |
| 4,102,339 | 7/1978 | Weber et al. | 606/105 |
| 4,341,206 | 7/1982 | Perrett et al. | 606/80 |
| 4,359,906 | 11/1982 | Cordey | 73/862 |
| 4,382,438 | 5/1983 | Jacobs | 606/61 |
| 4,484,570 | 11/1984 | Sutter et al. | 606/72 |
| 4,493,317 | 1/1985 | Klaue | 606/69 |
| 4,513,744 | 4/1985 | Klaue | 606/69 |
| 4,565,193 | 1/1986 | Sterli | 606/69 |
| 4,599,999 | 7/1986 | Klaue | 606/96 |
| 4,628,920 | 12/1986 | Mathys, Jr. et al. | 606/62 |
| 4,705,027 | 11/1987 | Klaue | 606/64 |
| 4,714,076 | 12/1987 | Comte et al. | 606/59 |
| 4,803,976 | 2/1989 | Frigg et al. | 606/97 |
| 4,817,591 | 4/1989 | Klaue | 606/64 |

*Primary Examiner*—Robert A. Hafer
*Assistant Examiner*—Michael Brown
*Attorney, Agent, or Firm*—Richards, Medlock & Andrews

[57] ABSTRACT

A bone fixation set for the treatment of distal radial fractures is provided. The device includes a plate having countersunk bone screw holes and a blade constructed for placement in the capitate of the radius. A method for implanting the bone fixation set is also provided.

17 Claims, 3 Drawing Sheets

DISTAL RADIAL FRACTURE SET AND METHOD FOR REPAIRING DISTAL RADIAL FRACTURES

BACKGROUND OF THE INVENTION

Fracture of the distal radius, commonly known as a Colles' fracture, is one of the most common fractures occurring in humans with frequency estimates ranging as high as 350,000 or more per year in the United States alone. Despite the high incidence of such fractures, there has been a tendency towards the relative neglect of patients with this fracture. As a result, many physicians find that patients suffering from distal radial fractures have persistent disability which is directly related to the failure to restore a normal anatomical configuration to the radial bone. Much of this failure can be attributed to the lack of a suitable device and process which would provide: (i) accurate open reduction; (ii) rigid internal fixation; and (iii) early active motion of the joint.

Colles' fractures have commonly been treated using standard immobilizing cast techniques. Such casts prevent movement of the radiocarpal joint throughout the course of rehabilitation. Further, such casts fail to provide adequate internal fixation to the radius, thereby resulting in a relatively high rate of deformity, pain, and prolonged disability.

Contemporary external fixation devices utilizing bone pins have provided some improvement in the management of severe fractures of the distal radius relative to simple plaster cast techniques. However, such external fixation devices represent only an interim step in the evolution of orthopedic management of this fracture. Numerous complications, including infection at the pin track sites, inability to maintain or obtain satisfactory reduction, joint stiffness, and prolonged periods of treatment and disability have been reported repeatedly.

SUMMARY OF THE INVENTION

The distal radial fracture set of the present invention includes a low profile fixation plate and a blade. The fixation plate is constructed to fit closely to the dorsal surface of the distal radius. A plurality of countersunk screw holes are formed through the plate, thereby permitting the plate to be secured to the bone such that the heads of the bone screws are flush with or below the upper surface of the plate. In this way, the fixation plate has an overall low profile and thus does not impede the movement of extensor tendons over the surface of the radius. In order to maintain the structural integrity of the fixation plate, the thickness of the plate is substantially constant along its length.

The blade of the present invention is attachable to the distal end of the fixation plate. Each blade includes an attachment portion and a blade insertion portion. When the fracture set of the present invention is secured to the radius, the blade extends from the plate into the sub-articular portion of the radius. In the case of severe fractures in which the radius is extremely comminuted, a plurality of blades can be attached to the plate.

The method of the present invention for treating a distal radial fracture includes the steps of extending and securing the hand and forearm in a fully extended position, for example, through the use of a fingertrap traction device, thereby reducing the fracture. Fragments of the comminuted bone are then returned to their anatomically corrected positions and, if necessary, bone pins and/or bone grafts are used to restore the integrity of the radius. The radius is then prepared for affixation of the distal radial fracture set of the present invention. This preparation process includes the steps of drilling bone screw holes through the distal surface of the radius, creating recessed areas in the radius about the bone screws holes, and cutting a groove in the sub-articular portion of the radial bone. A template can be used in order to facilitate the proper orientation of the bone screw holes, recesses, and the groove. The fixation plate of the fracture set is then secured with bone screws to the dorsal surface of the radius. When desired, the blade is inserted through the sub-articular portion of the radius and attached to the plate. Any temporary pins or wires used to secure random bone fragments are then removed.

DETAILED DESCRIPTION

Figure 1:
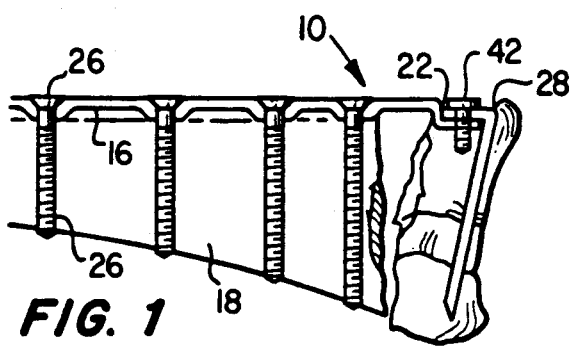
FIG. 1 is a partial cross-sectional view of a preferred embodiment of the distal radial fracture set of the present invention in place on a fractured radius.
Figure 2:
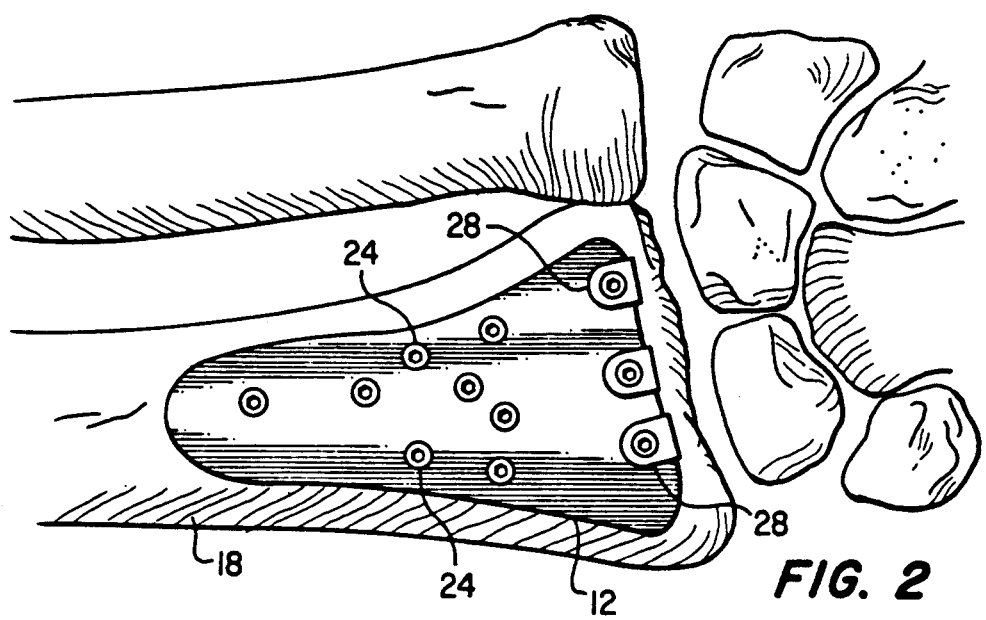
FIG. 2 is an overall plan view of the preferred embodiment of the distal radial fracture set of the present invention.
Figure 4:
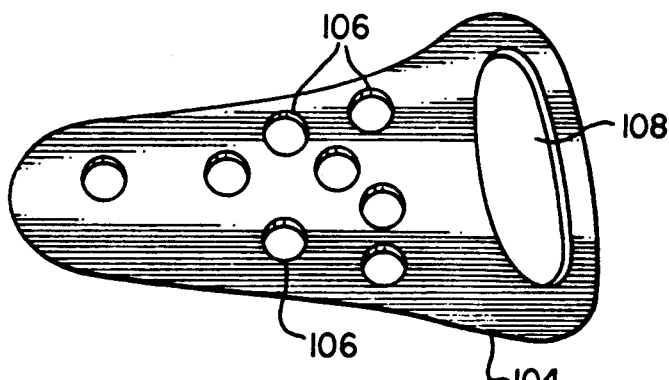
FIG. 4 is an overall plan view of the template for use in applying the distal radial fracture set of the present invention.

A distal radial fracture set is generally indicated at 10 of FIGS. 1 and 2. Fixation plate 12 of set 10 has an upper surface 14 and a lower surface 16. Plate 12 is constructed to provide a close fit between lower surface 16 and the dorsal surface of radius bone 18.

Plate 12 has a proximal end 20 and a distal end 22. As best seen in FIG. 2, distal end 22 has a greater width than proximal end 20. In this way, plate 12 is able to provide greater stability to the fractured radius at the location of the fracture, i.e., at the distal end of the radius. However, it is to be appreciated that plate 12 can be of any shape without departing from the scope of the present invention.

Figure 1A:
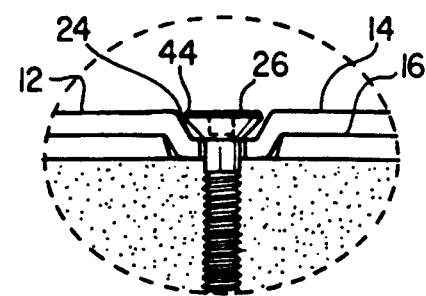
FIGURE 1a is an exploded view of a countersunk hole of the fracture set depicted in FIG. 1.

A plurality of bone screw holes 24 are formed through plate 12. As best seen in FIGURE 1a, the dimension of bone screw hole 24 decreases from upper surface 14 to lower surface 16 of plate 12. In this way, bone screw 26 can be countersunk through plate 12, thereby creating a low profile for set 10. In a preferred embodiment of the present invention, the thickness of plate 12 between upper surface 14 and lower surface 16 is approximately 2-3 mm. In addition, plate 12 can be constructed of any known biocompatible material such as titanium or stainless steel.

Both upper surface 14 and lower surface 16 are depressed in the region of bone screw holes 24. This feature further enables plate 12 to have a very low profile, thus creating only minimal interference between plate 12 and the extensor tendons in the wrist. In addition, the low profile of plate 12 allows for better closure of the soft tissues of the wrist following surgery. In the preferred embodiment depicted in FIG. 1a, plate 12 has a substantially constant thickness along its length, including those depressed regions which are proximate bone screw holes 24. Thus, plate 12 is able to provide adequate support to the fractured radius.

Figure 3:
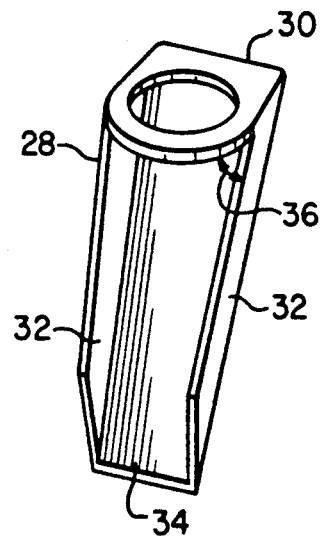
FIG. 3 is an elevational view of a blade of the distal radial fracture set of a preferred embodiment of the present invention.

In a preferred embodiment, fixation set 10 includes a plurality of blades 28. Each blade 28 includes an attachment portion 30 and a blade insertion portion 34. In another preferred embodiment depicted in FIG. 3, blade 28 includes two support wings 32. It will be appreciated that the structural strength of blade 28 is increased by the presence of wings 32. That is, support wings 32 provide added structural stability to blade insertion portion 34 in accordance with the basic I-beam principle. However, blade 28 may assume numerous configurations without departing from the spirit and scope of the invention. Insertion portion 34 of blade 28 provides a compression effect between the comminuted portions of radius 18 and the remaining sections of that bone. In addition, blade 28 provides support for the radial bone fragments commonly occurring in distal radial fractures.

A plurality of blades 28 preferably are used when the radius is extensively comminuted, thereby making it difficult to retain the bone fragments through the use of standard bone screws. Blades 28, and more particularly insertion portions 34, provide a broad support structure to aid in the healing of the comminuted radius. In combination with fixation plate 12, blade 28 provides a low profile, highly effective fracture set for restoring a normal anatomical configuration to the radius and to the surrounding tissues.

Insertion portions 34 and support wings 32 extend angularly from attachment section 30. In a preferred embodiment, angle 36 between support wings 32 and attachment section 30 measures between 60° and 120°. However, it is to be appreciated that the magnitude of angle 36 is primarily dependent upon the dimensions of the bone and the nature of the fracture. Accordingly, there may be circumstances under which it is desirable to provide a blade 28 have an angle 36 outside this 60°-120° range.

Blade 28 is constructed to be inserted into the capitate of the radius. It is to be appreciated that plate 12 can be efficaciously used with or without the presence of blade 28. It is also to be appreciated that one or more of blades 28 can be used in conjunction with plate 12. For example, FIG. 2 depicts an embodiment of the present invention in which three blades 28 have been attached to plate 12. In this embodiment, the use of a plurality of blades provides additional support and compression to the comminuted portions of the fractured distal radius.

Attachment section 30 of blade 28 defines a retaining screw hole 38. Retaining holes 40 are formed at the distal end 22 of plate 12 to accommodate attachment of blades 28. Blade 28 can be secured to plate 12 by means of a screw 42 driven through screw hole 38 of blade 28 and retaining hole 40 of plate 12, as best seen in FIG. 1. In a preferred embodiment, upper surface 14 and lower surface 16 are depressed about retaining holes 40. Accordingly, the overall profile of fixation set 10 remains low when blade 28 is attached to plate 12.

Bone screws 26 preferably are sized to be driven substantially through radius bone 18 whereby plate 12 and blade 28 can be securely affixed to radius 18. Screws 26 should have a sufficient length to be anchored in the cortex of ventral surface of the bone. In addition, head 44 of bone screw 26 preferably has a configuration permitting it to substantially mate with bone screw holes 24. As discussed above, bone screws 26 are configured to be countersunk through bone screw holes 24 in order to minimize interference with the movement of the extensor tendons and to provide better closure of the soft tissues in the wrist.

Figure 5A:
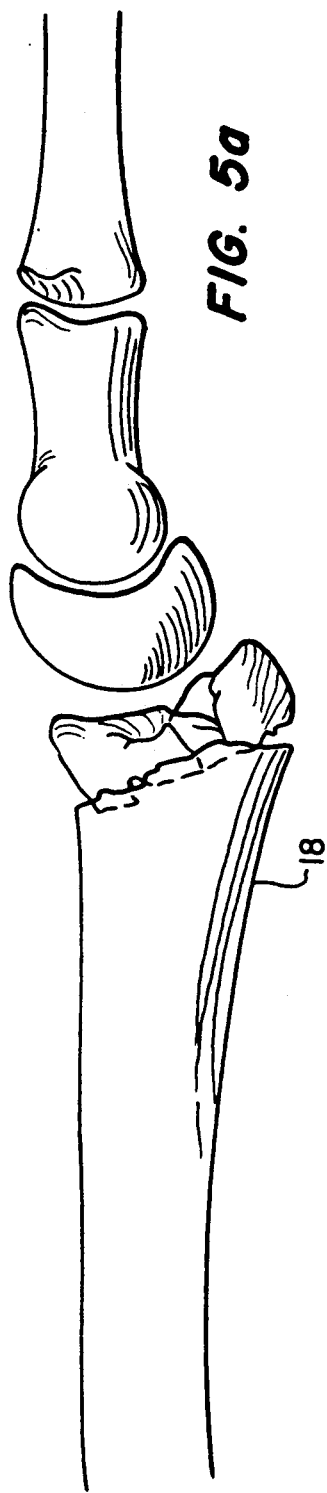
FIG. 5a is a schematic view of the distal portion of a fractured radius prior to the application of a reduction force and the repositioning of fragmented bone.
Figure 5B:
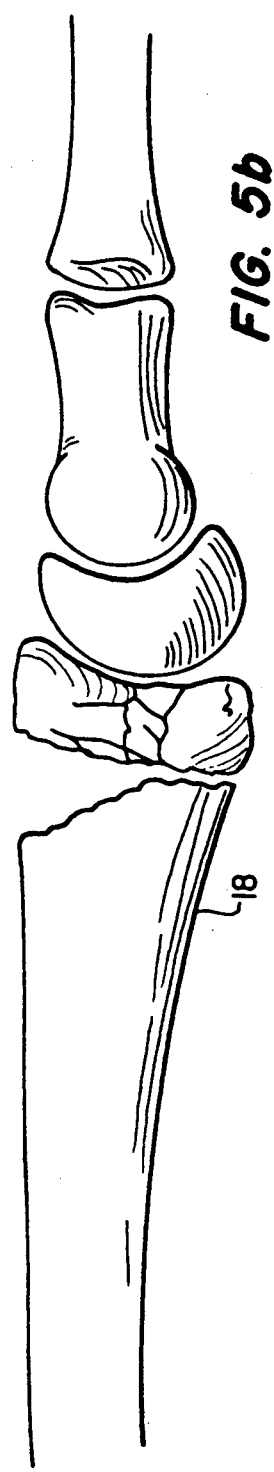
FIG. 5b is a schematic view of a fractured radius after reduction of the fracture.
Figure 5C:
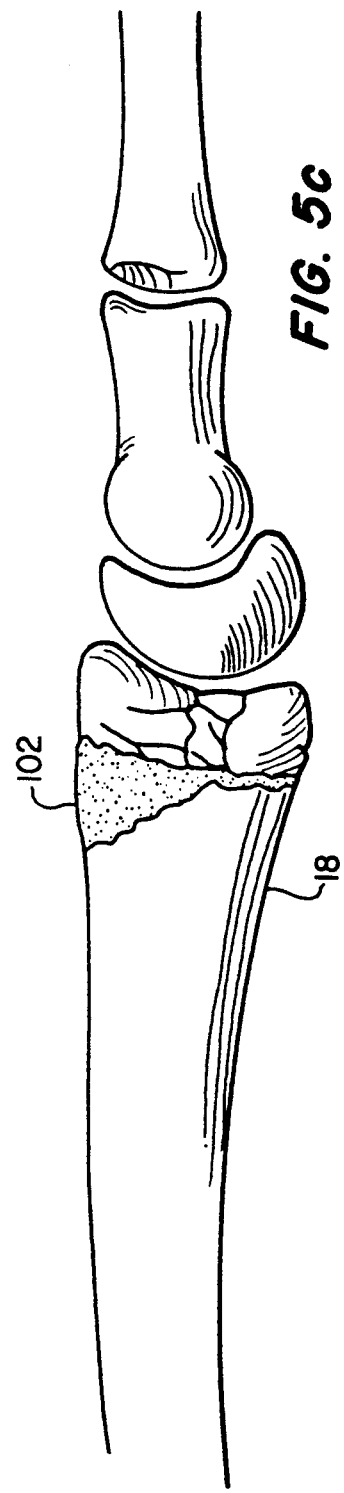
FIG. 5c is a schematic view of a fractured radius following the repositioning of bone fragments and the application of artificial bone material.
Figure 6:
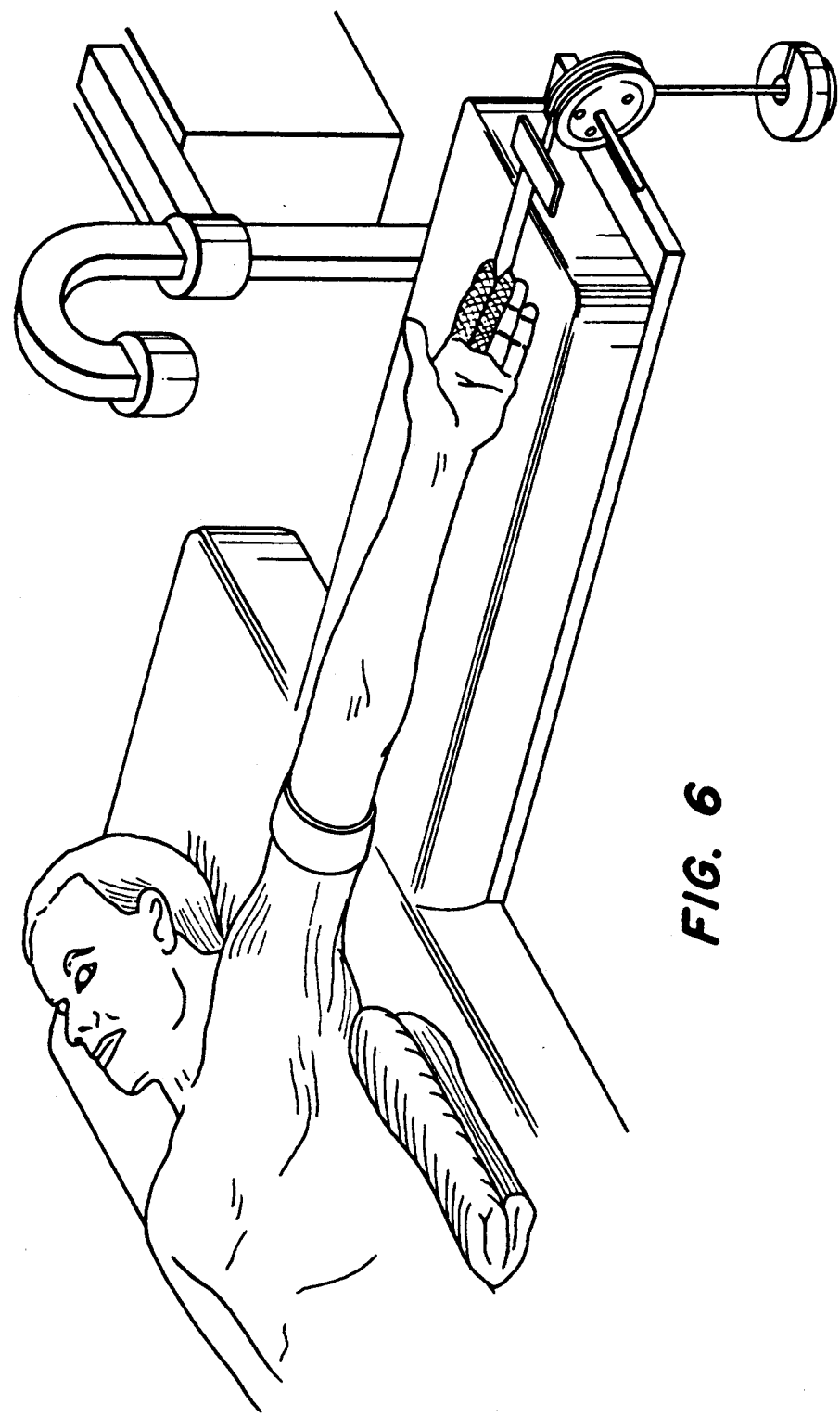
FIG. 6 is a schematic view of a patient being treated using a fingertrap traction device and the method of the present invention.

The method for repairing distal radial fractures of the present invention includes the initial step of placing the arm of the patient in an extended position on an operating surface. For example, as depicted in FIG. 6, the patient's arm is placed flat on an operating surface with the palm facing upward. The hand and forearm are thus readily accessible to the physician. In order to maintain the extended condition of the hand and forearm throughout the course of the process described herein, a fingertrap traction system is used. As depicted in FIG. 6, fingertraps are placed about the index and middle fingers and a weight is applied to the traction system. Ten (10) pounds has been found to be an appropriate amount of traction force positions. Extension of the hand and forearm results in a reduction of the fracture, as best seen in FIGS. 5a –c. A distal radial fracture results in the translocation of the bones within the wrist as depicted in FIG. 5a. FIG. 5b depicts the same hand and forearm following reduction of the fracture. Following reduction, the orientation of the carpals to the radius and ulna is restored to its proper anatomical condition. Again, the reduction force applied by the traction is to be maintained in order to retain the bones in this corrected anatomical configuration.

After the fracture has been properly reduced, the skin is surgically opened and the fracture is exposed. In some cases it will be necessary to utilize a temporary, rigid external fixator in order to retain the hand and wrist in their extended positions. An external fixator can be removably affixed to the index finger and the radius in order to retain a fixed distance between the carpus bones during repair.

Following reduction of the fracture, it is desirable to reposition any bone fragments resulting from the fracture. Such fragments are particularly common in the case of distal radial fractures. If necessary, these fragments can be temporarily retained in their anatomically correct positions through the use of any known fixation method, including the use of K-wires or bone screws.

Following the repositioning of the comminuted bone fragments of the radius, it may be desirable to provide a bone graft in order to restore the integrity of the radius. As best seen in FIG. 5c, bone graft 102 is provided in order to restore the configuration of the radius. The iliac bone commonly is used in a bone graft of this type. However, this procedure requires a separate incision on the patient's iliac crest and the use of a general anesthesia. An alternative procedure would use artificial bone material in lieu of such a bone graft. For example, calcium apitite crystal fragments can be used to augment the comminuted fragments of the fractured radius.

Following reorientation of the radius and carpus bones, bone screw guide holes are drilled through the radius from the dorsal to the ventral surfaces. Recesses are formed about the bone screw guide holes using a specially designed drill bit. These recesses are dimensioned to receive the depressed regions of the plate 12 described in detail above. In a preferred embodiment of the process of the present invention, a template 104 is provided for use in creating the bone screw holes in order to ensure their proper orientation relative to one another. Template 104 has a plurality of bone screw hole guides 106 formed therethrough. Bone screw hole guides 106 have a diameter substantially greater than the diameter of bone screws 26 in order to facilitate the formation of recesses about bone screw holes 24. In this embodiment, template 104 is used during the formation of the countersunk recesses proximal each of the bone screw holes.

Once the bone screw holes and countersunk recesses have been formed in the radius bone, the bone fixation plate described in detail above can be affixed to the fractured radius with bone screws. It will be appreciated that the bone fixation plate and the bone screws used in this procedure can be manufactured of any biocompatible material. However, it has been found to be particularly desirable to utilize titanium in the construction of the bone fixation plate and bone screws of the present invention. Titanium provides both the desired level of biocompatibility and the appropriate flexural strength in order to facilitate the healing of the fractured radius as well as the surrounding tissues.

If the fracture is particularly unstable and comminuted such that screw fixation of the distal radial fragments is not practical, bone fixation blades of the type described in detail are used. In this instance, a groove is formed along the dorsal surface of the capitate of the radius in order to remove the cortex, i.e. the hard exterior surface of the bone Template 104 is also used to facilitate the proper orientation of this groove. Opening 108 is provided on template 104 for this purpose. The blades are then inserted into the intra-articular portion of the radius by tapping them through the cancellous bone of the radius. The blade is then attached to the bone fixation plate as discussed above.

If an external bone fixator has been used, it is removed following the affixation of the bone fixation plate and the bone fixation blades. Next, the surgical incision is closed and the forearm is wrapped with a bulky dressing until the initial swelling has subsided. When the incision has healed, early radiocarpal joint motion can be initiated. Under normal conditions joint motion can be started in only a few days as a result of the accurate reduction and fixation capabilities of the present invention.

Although the bone fixation plate and method of the present invention have been described in detail herein with respect to particular preferred embodiments, it will be evident that various and further modifications are possible without departing from the spirit and scope of the present invention.

I claim:

1. A bone fixation set for the treatment of distal radial fractures comprising:
    a fixation plate, said plate having a plurality of bone screw holes formed therethrough, said plate having a proximal end and a distal end, said plate having an upper surface and a lower surface, said lower surface of said plate constructed to substantially conform to the dorsal surface of the radius bone, said upper surface and said lower surface of said plate being depressed proximate said bone screw holes formed through said plate; and
    an attachable blade, said blade comprising a blade insertion portion and an attachment portion, said attachment portion of said blade being attachable to said distal end of said plate.

2. The bone fixation set for the treatment of distal radial fractures of claim 1, wherein a wing section extends substantially perpendicularly from said blade insertion portion.

3. The bone fixation set for the treatment of distal radial fractures of claim 1, wherein said bone fixation set comprises a plurality of attachable blades.

4. The bone fixation set for the treatment of distal radial fractures of claim 1, wherein said upper surface and said lower surface of said plate are depressed at the distal end of said plate, whereby said bone fixation set has a low profile along its length.

5. The bone fixation set for the treatment of distal radial fractures of claim 1, wherein said distal end of said plate and said attachment portion of said blade have holes formed therethrough whereby said blade can be attached to said plate by placing a retaining screw through said holes defined through said attachment portion of said blade and said distal end of said plate.

6. The bone fixation set for the treatment of distal radial fractures of claim 1, wherein said plurality of bone screw holes formed through said plate have a decreasing dimension from said upper surface to said lower surface whereby a bone screw can be countersunk through each said bone screw hole.

7. The bone fixation set for the treatment of distal radial fractures of claim 1, wherein said plate decreases in width from said distal end to said proximal end of said plate.

8. The bone fixation set for the treatment of distal radial fractures of claim 1, further comprising a plurality of bone screws, said bone screws being constructed to be countersunk through said bone screw holes formed on said plate.

9. The bone fixation set for the treatment of distal radial fractures of claim 1, wherein said plate has a substantially constant thickness.

10. A method for repairing a distal radial fracture comprising:
    extending the hand and forearm such that said hand and said forearm are extended to their full lengths, thereby reducing the fracture;
    repositioning radial bone fragments to their proper anatomical positions within said forearm;
    drilling screw holes through said radial bone;
    forming concave depressions in said radial bone about each of said screw holes;
    threadably securing a bone fixation plate to said radial bone by driving bone screws through said bone fixation plate and into said fractured radius.

11. The method for repairing a distal radial fracture of claim 10, wherein said method further comprises removably attaching an external fixator to the index finger and the radial bone whereby the hand and forearm are temporarily fixed in their extended positions.

12. The method for repairing a distal radial fracture of claim 11, wherein said method further comprises removing said external fixator from the index finger and the radial bone subsequent to securing the bone fixation plate to the fractured radius.

13. The method for repairing a distal radial fracture of claim 10, wherein said method further comprises temporarily pinning said radial bone fragments whereby said fragments are retained in their proper anatomical positions prior to drilling screw holes through said radial bone.

14. The method for repairing a distal radial fracture of claim 13, wherein said method further comprises removing the temporary pins used to pin radial bone fragments in their corrected positions subsequent to securing said bone fixation plate to said radial bone.

15. The method for repairing a distal radial fracture of claim 10, wherein said method further comprises:
   cutting a groove in the cortex of the capitate of said radial bone, said groove being dimensioned to receive a blade of a bone fixation set;
   inserting said blade through the groove formed in the capitate of said radial bone and into said radial bone; and
   securing said blade to said bone fixation plate.

16. A method for repairing a distal radial fracture comprising:
   extending the hand and forearm such that said hand and said forearm are extended to their full lengths, thereby reducing the fracture;
   repositioning radial bone fragments to their proper anatomical positions within said forearm;
   drilling bone screw holes through said radial bone;
   cutting a groove in the cortex of the capitate of said radial bone, said groove being dimensioned to receive a blade of a bone fixation set;
   threadably securing a plate of a bone fixation set to said radial bone by driving bone screws through said plate and into said fractured radius;
   inserting said blade through said groove formed in the capitate of said radial bone and into said radial bone; and
   securing said blade to said plate of said bone fixation device.

17. A low-profile bone fixation plate for the treatment of fractures comprising:
   a bone fixation plate having a plurality of bone screw openings formed therethrough for receiving bone screws, said plate having an upper surface and a lower surface, said upper surface and said lower surface being depressed toward one another proximate said bone screw openings, wherein said bone screw openings taper inwardly from said upper surface to said lower surface whereby bone screws implanted in the bone are recessed within the fixation plate.

* * * * *

UNITED STATES PATENT AND TRADEMARK OFFICE
CERTIFICATE OF CORRECTION

PATENT NO. : 5,006,120
DATED : April 9, 1991
INVENTOR(S) : Peter R. Carter It is certified that error appears in the above-identified patent and that said Letters Patent is hereby corrected as shown below:

Column 1, after the title of the invention, please insert
--TECHNICAL FIELD OF THE INVENTION This invention relates to a device for the treatment of bone fractures, particularly distal radial fractures, and a method for treating such fractures.--

In the Detailed Description -

Column 4, line 29 - after "force" insert --to retain the hand and forearm in their extended--

Column 5, line 36 - after "bone" insert --.--

Signed and Sealed this

Twenty-second Day of September, 1992

*Attest:*

DOUGLAS B. COMER

*Attesting Officer*     *Acting Commissioner of Patents and Trademarks*